(12) United States Patent
Lewis et al.

(10) Patent No.: US 7,461,574 B2
(45) Date of Patent: Dec. 9, 2008

(54) MULTIPLE SCREW DELIVERY APPARATUS

(75) Inventors: Derek S. Lewis, Jacksonville, FL (US); Shawn D. Roman, Orange Park, FL (US)

(73) Assignee: Biomet Microfixation, LLC, Jacksonville, FL (US)

( * ) Notice: Subject to any disclaimer, the term of this patent is extended or adjusted under 35 U.S.C. 154(b) by 645 days.

(21) Appl. No.: 10/833,260

(22) Filed: Apr. 27, 2004

(65) Prior Publication Data

US 2004/0243139 A1   Dec. 2, 2004

Related U.S. Application Data

(60) Provisional application No. 60/466,394, filed on Apr. 28, 2003.

(51) Int. Cl.
  *B25B 23/06* (2006.01)
  *A61B 17/56* (2006.01)
(52) U.S. Cl. .................. 81/57.37; 606/104; 81/431
(58) Field of Classification Search ............. 81/57.37, 81/431, 433, 435; 606/104, 73, 143
See application file for complete search history.

(56) References Cited

U.S. PATENT DOCUMENTS

| | | | |
|---|---|---|---|
| 2,247,500 A * | 7/1941 | Hutchison, Jr. ............ 81/431 |
| 2,248,054 A | 7/1941 | Becker |
| 3,010,193 A | 11/1961 | Croall, Jr. et al. |
| 3,511,286 A * | 5/1970 | Brauchla ................ 81/431 |
| 3,528,466 A | 9/1970 | Tracy |
| 3,604,487 A | 9/1971 | Gilbert |
| 4,140,111 A * | 2/1979 | Morrill ................ 606/104 |
| 4,244,246 A * | 1/1981 | Gillett ................ 81/125 |
| 4,539,872 A | 9/1985 | Bochman, Jr. |
| 4,667,545 A | 5/1987 | Gould, Jr. et al. |
| 4,936,169 A | 6/1990 | Parsons |
| 4,998,452 A | 3/1991 | Blum |
| 5,169,400 A | 12/1992 | Muhling et al. |
| 5,231,902 A | 8/1993 | Uno et al. |
| 5,268,001 A * | 12/1993 | Nicholson et al. ........... 606/104 |
| 5,275,601 A | 1/1994 | Gogolewski et al. |
| 5,314,989 A | 5/1994 | Kennedy et al. |
| 5,337,636 A | 8/1994 | Shea |
| 5,403,347 A | 4/1995 | Roby et al. |
| 5,431,679 A | 7/1995 | Bennett et al. |
| 5,445,641 A | 8/1995 | Frigg et al. |
| 5,470,334 A | 11/1995 | Ross et al. |
| 5,484,440 A | 1/1996 | Allard |
| 5,484,451 A | 1/1996 | Akopov et al. |
| 5,502,159 A | 3/1996 | Liu et al. |

(Continued)

FOREIGN PATENT DOCUMENTS

JP   38-25793   11/1963

(Continued)

*Primary Examiner*—Hadi Shakeri
(74) *Attorney, Agent, or Firm*—Harness, Dickey & Pierce, P.L.C.

(57) ABSTRACT

A multiple screw dispensing apparatus and method for surgical applications includes a body and a screw set loaded within the body. The screw set includes a plurality of releasably coupled screws. A block is slidably mounted with respect to the body and abuts a head portion of the screw. After driving a screw into a material, another screw may be positioned for use by engaging the block.

20 Claims, 14 Drawing Sheets

U.S. PATENT DOCUMENTS

| | | | |
|---|---|---|---|
| 5,531,143 A | 7/1996 | Habermehl et al. | |
| 5,538,423 A | 7/1996 | Coss et al. | |
| 5,575,054 A | 11/1996 | Klinzing et al. | |
| 5,584,221 A | 12/1996 | Petrantoni | |
| 5,601,573 A * | 2/1997 | Fogelberg et al. | 606/143 |
| 5,626,585 A * | 5/1997 | Mittelstadt et al. | 606/143 |
| 5,628,751 A | 5/1997 | Sander et al. | |
| 5,653,710 A | 8/1997 | Harle | |
| 5,662,658 A | 9/1997 | Wenstrom, Jr. | |
| 5,690,639 A | 11/1997 | Lederer et al. | |
| 5,695,497 A | 12/1997 | Stahelin | |
| 5,735,854 A | 4/1998 | Caron et al. | |
| 5,827,287 A | 10/1998 | Tunc | |
| 5,830,221 A | 11/1998 | Stein et al. | |
| 5,860,983 A | 1/1999 | Wenstrom, Jr. | |
| 5,888,200 A | 3/1999 | Walen | |
| 5,911,722 A | 6/1999 | Adler et al. | |
| 5,928,244 A | 7/1999 | Tovey et al. | |
| 5,971,987 A | 10/1999 | Huxel et al. | |
| 5,988,026 A | 11/1999 | Reckelhoff et al. | |
| 6,132,435 A | 10/2000 | Young | |
| 6,183,478 B1 | 2/2001 | Konieczynski | |
| 6,189,422 B1 | 2/2001 | Stihl | |
| 6,273,893 B1 | 8/2001 | McAllen, III et al. | |
| 6,283,973 B1 | 9/2001 | Hubbard et al. | |
| 6,322,563 B1 | 11/2001 | Cummings et al. | |
| 6,328,746 B1 | 12/2001 | Gambale | |
| 6,402,759 B1 | 6/2002 | Strong et al. | |
| 7,105,000 B2 * | 9/2006 | McBrayer | 606/143 |
| 7,147,641 B2 * | 12/2006 | Chen | 606/104 |
| 2001/0021853 A1 | 9/2001 | Heckele et al. | |
| 2002/0052607 A1 | 5/2002 | Kennefick et al. | |

FOREIGN PATENT DOCUMENTS

| | | |
|---|---|---|
| JP | 2002-519136 | 3/2001 |
| JP | 2002511279 | 4/2002 |
| JP | 2002527187 | 8/2002 |
| WO | WO 02/096310 | 12/2002 |

* cited by examiner

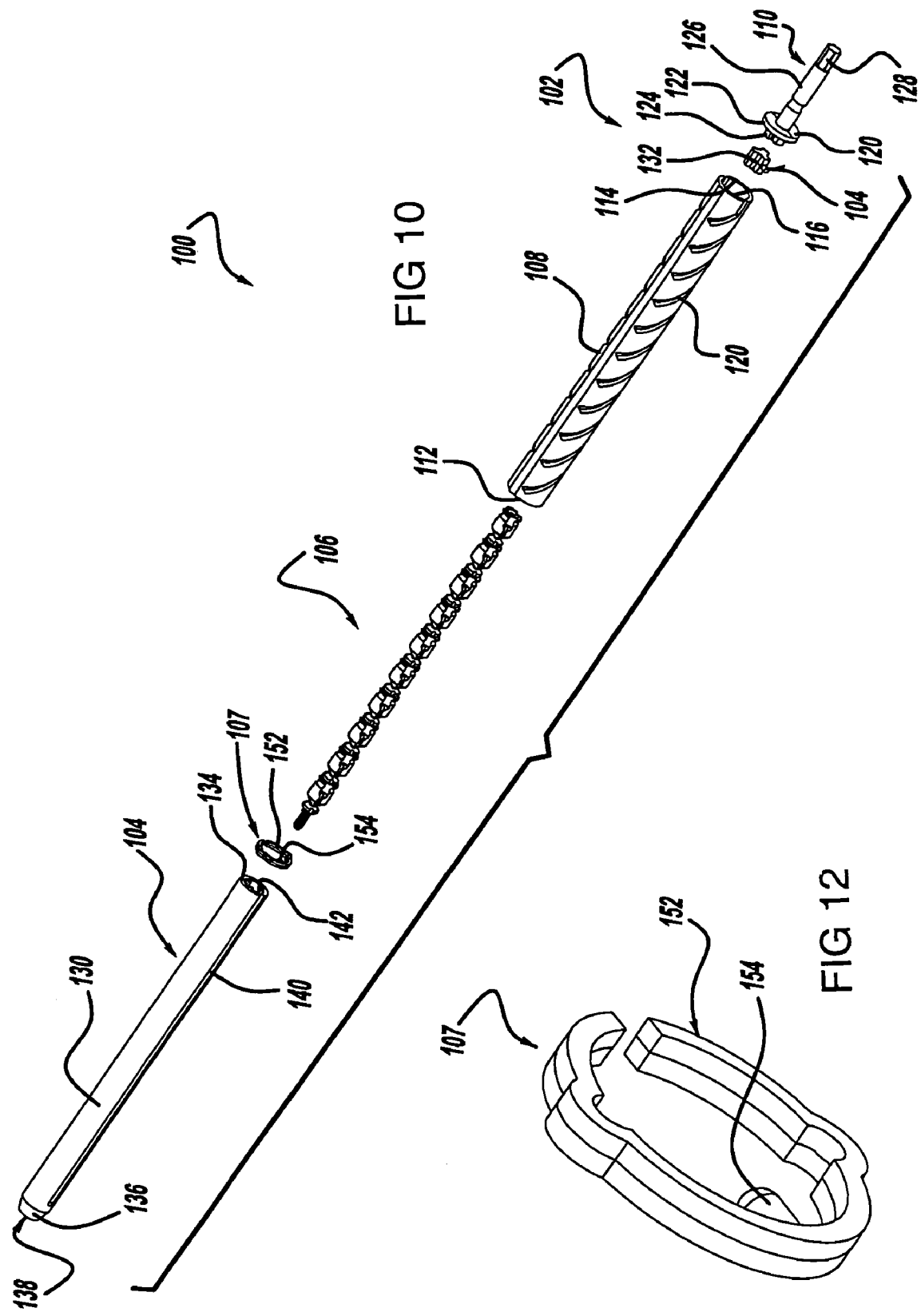

MULTIPLE SCREW DELIVERY APPARATUS

CROSS-REFERENCE TO RELATED APPLICATIONS

This application claims the benefit of U.S. Provisional Application No. 60/466,394, filed on Apr. 28, 2003. The disclosure of the above application is incorporated herein by reference.

FIELD OF THE INVENTION

The present teachings relate to a surgical application for the repair of bone fractures and deformities.

BACKGROUND

Bone fractures and bone deformities are common problems encountered in the medical field. A typical method for dealing with these ailments involves fixing bone segments together using surgical screws. These surgical screws, whether permanent or bio-absorbable, must be sterilized prior to insertion into the body.

Typically, a screwdriver or other powered tool having a blade at one end is used to implant the surgical screws. The blade is designed to receive a screw for insertion into the bone. Currently, surgical screws are provided in implant containers that are sterilized by the hospital. An individual screw is loaded into the blade and inserted into the bone segment one at a time. Between each insertion, the user must retrieve a screw from the implant container and fix it to the blade.

While this method is acceptable, there are inefficiencies when the screw is fixed to the blade, such as mishandling or misalignment of the screw. Moreover, the time it takes to individually load the surgical screws into the blade increases the surgery time and the typical risks associated with surgery.

SUMMARY

A multiple screw dispensing apparatus and method for surgical applications is provided comprising a body and a screw set loaded within the body. The screw set includes a plurality of screws. A block is slidably mounted with respect to the body and abuts a head portion of the screw, whereby successive screws can be positioned for insertion of the screw into a material.

Further areas of applicability will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The invention will become more fully understood from the detailed description and the accompanying drawings, wherein:

FIG. 10 is an exploded perspective view of the multiple screw delivery apparatus of FIG. 9;

FIG. 12 is a perspective view of a stopper ring shown in FIG. 10;

DETAILED DESCRIPTION OF THE PREFERRED EMBODIMENTS

The following description is merely exemplary in nature and is in no way intended to limit the present teachings, their application, or uses.

Figure 1:
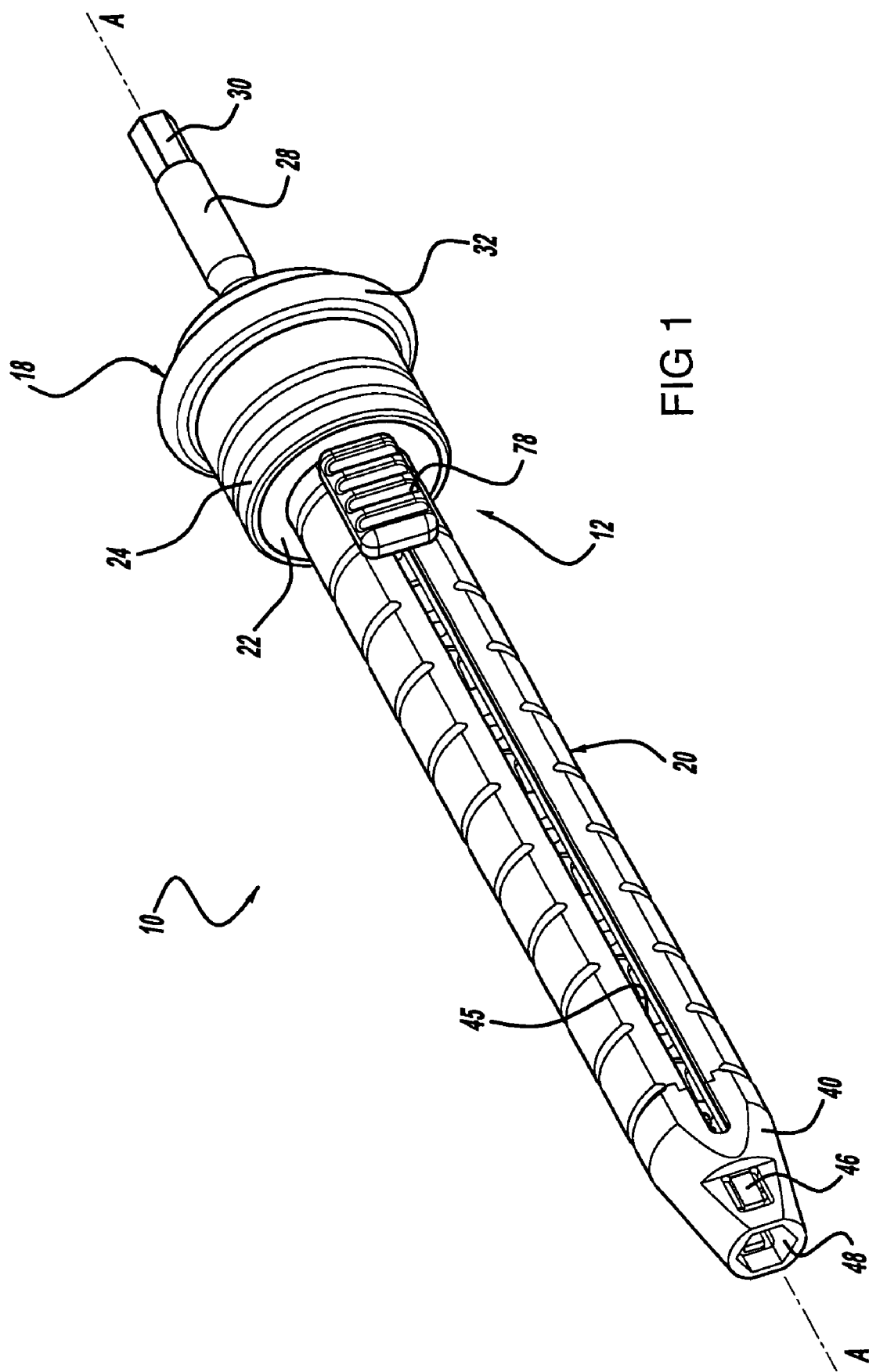
FIG. 1 is a perspective view of a multiple screw delivery apparatus constructed according to the present teachings.
Figure 2:
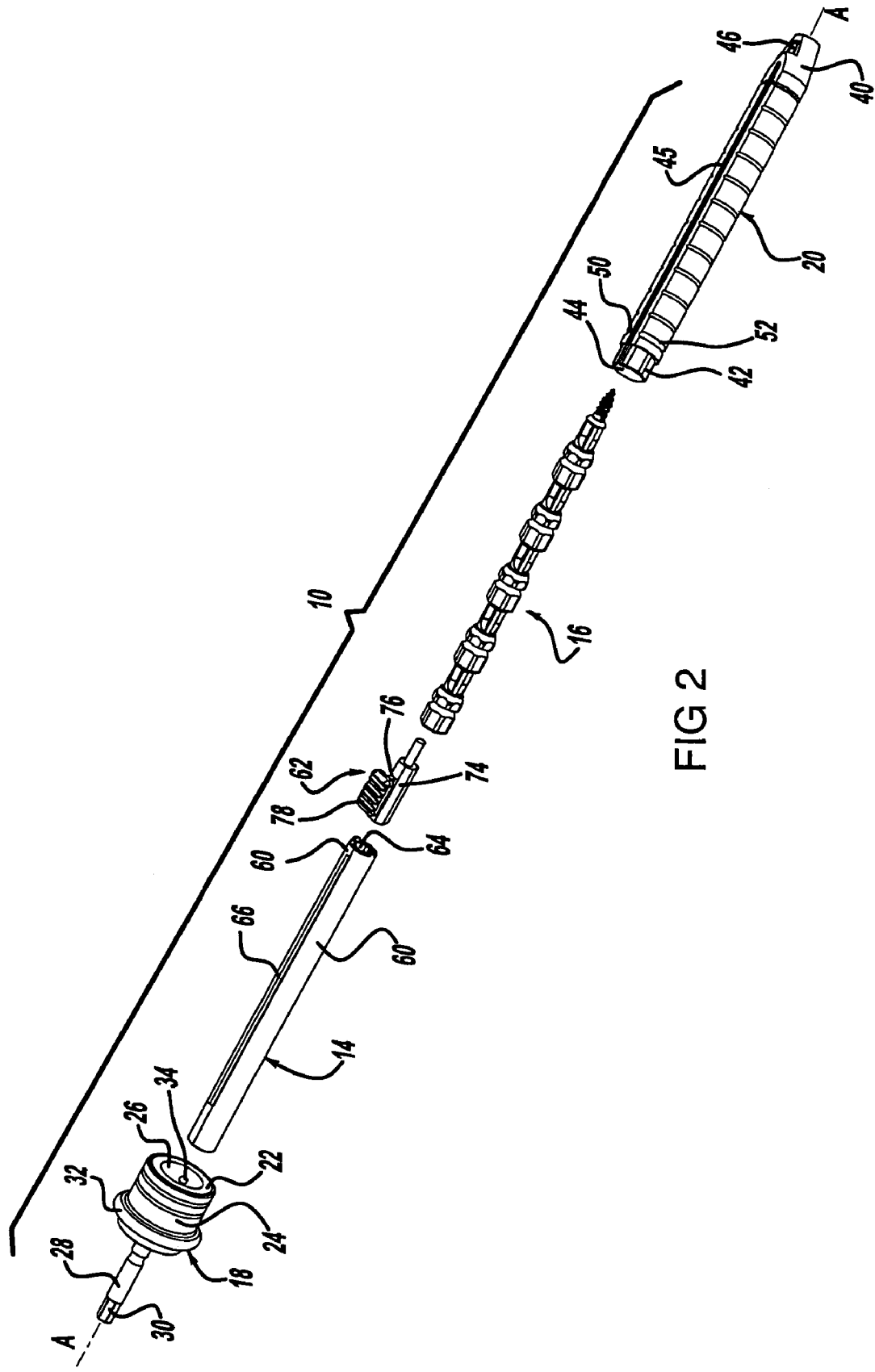
FIG. 2 is an exploded perspective view of the multiple screw delivery apparatus of FIG. 1.

With reference to FIGS. 1 and 2, there is illustrated a multiple screw delivery apparatus 10 including a body 12 having a longitudinal axis indicated by line A-A. The body 12 is sized to receive a clip 14. A plurality of screw-blade sets 16 are sized to fit within the clip 14. Engagement of the clip 14 urges the screw-blade sets 16 to be positioned for use and subsequently ejected from the body 12.

The body 12 includes a cap 18 and a tubular body 20. The cap 18 includes an inner body 22 mounted within a sleeve 24. The inner body 22 defines an opening 26 at one end sized to receive a portion of the tubular body 20. A drive shaft 28 extends out from an opposite end of the inner body 22 along axis A-A. The drive shaft 28 has a hexagonally shaped end 30 adapted to be received by a tool. The sleeve 24 is free to translate with respect to the inner body 22 along the axis A-A, and includes a flange 32 extending perpendicular to axis A-A along the circumference of the sleeve 24 to act as a grip for a user of the delivery apparatus 10.

Figure 4:
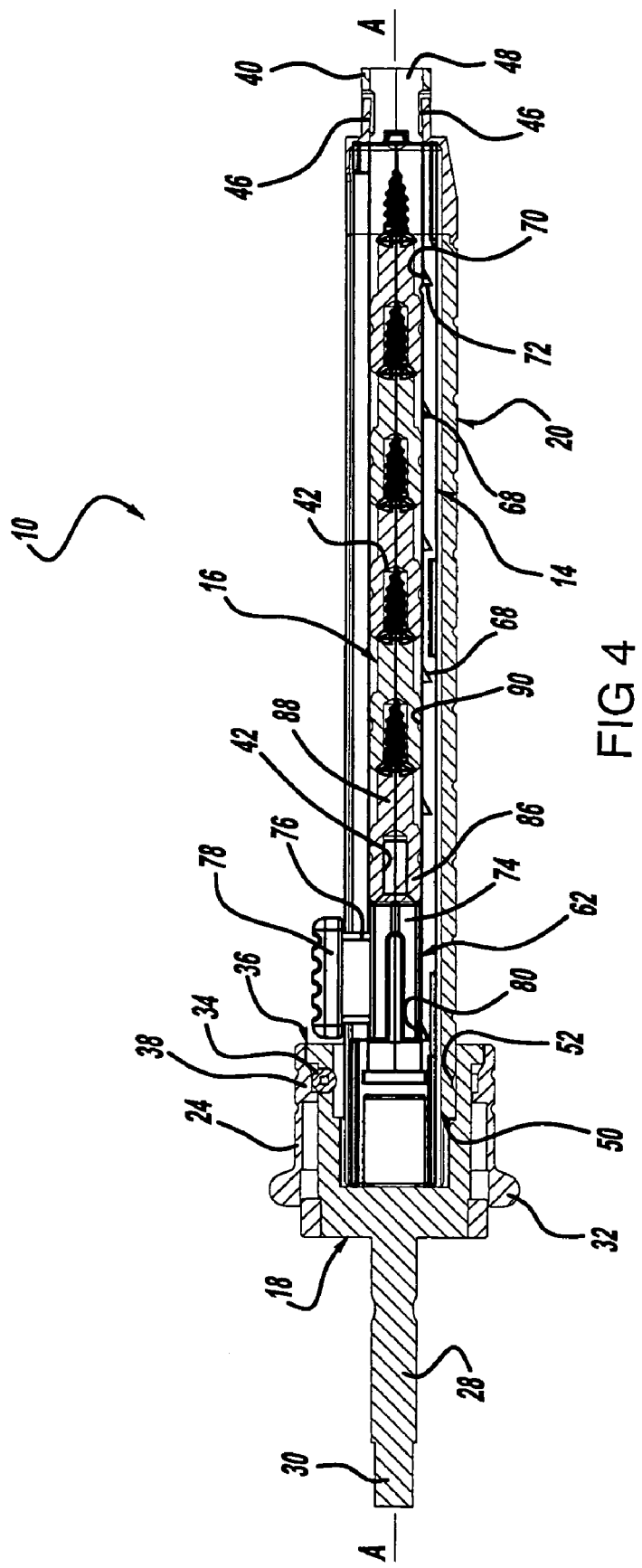
FIG. 4 is a cross-sectional view of the multiple screw delivery apparatus taken along line 4-4 in FIG. 1.
Figure 5:
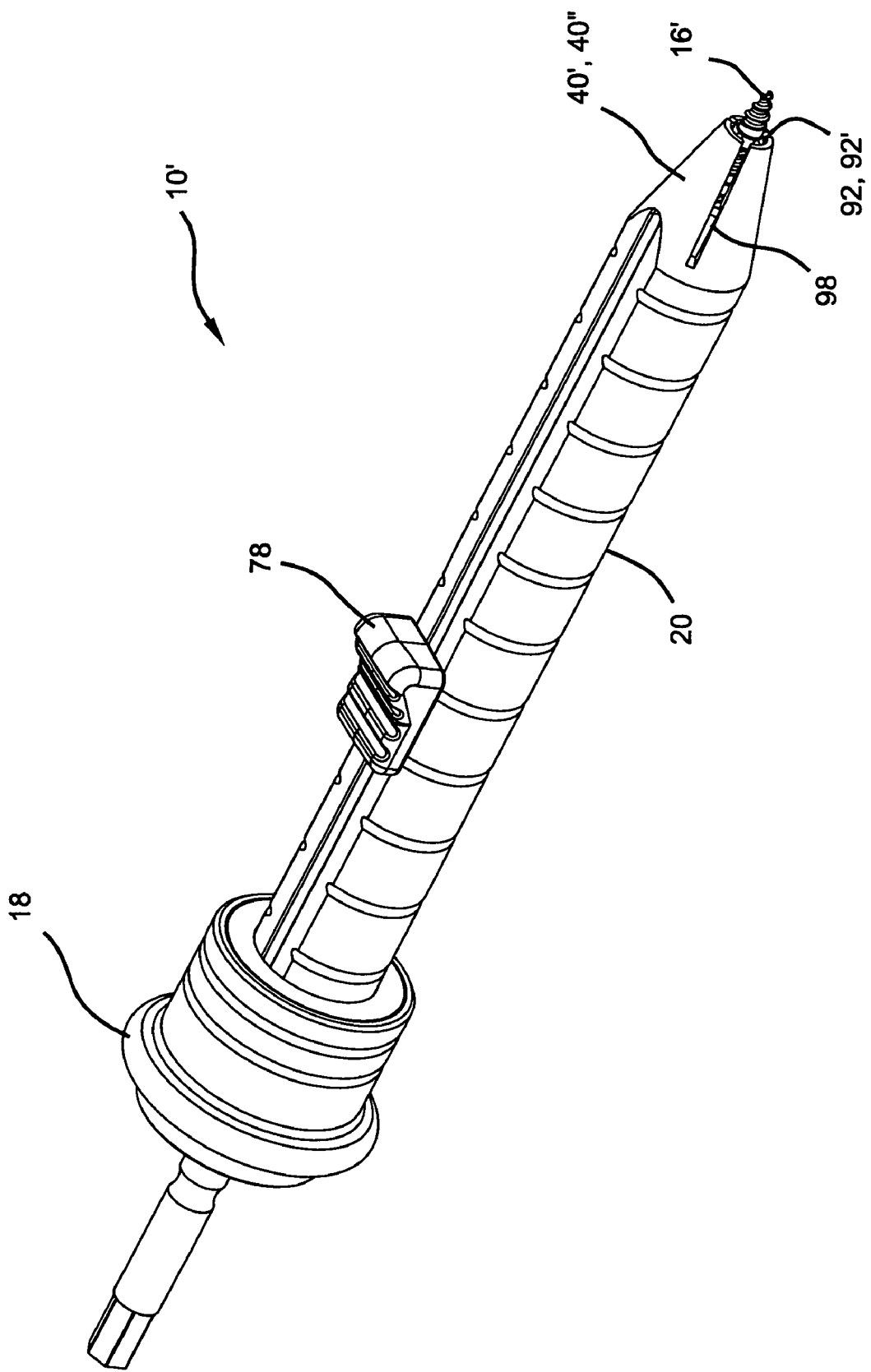
FIG. 5 is a perspective view of a multiple screw delivery apparatus according to the present teachings.

With reference to FIG. 4, the inner body 22 includes a plurality of ball detents 34 mounted along an outer surface. The ball detents 34 sit within detent slots 36 that extend into the opening 26. The sleeve 24 includes a projection 38 extending along the circumference of the inner surface of the sleeve 24. When the projection 38 and the ball detents 34 are in alignment, the projection 38 urges the ball detents 34 within the detent slots 36 such that the ball detents 34 partially extend into the opening 26 where they may engage a portion of the tubular body 20.

Returning to FIGS. 1 and 2, the tubular body 20 includes a dispensing end 40 and a cap end 42. The tubular body 20 further defines a bore 44 that extends from the dispensing end 40 to the cap end 42 along axis A-A. The bore 44 is sized to receive the clip 14. A longitudinal slot 45 extends from the outer surface of the tubular body 20 into the bore 44 and runs from the insertion end 40 to near the dispensing end 42 along axis A-A. The longitudinal slot 45 is sized to receive a portion of the clip 14 as will be described in greater detail below.

The dispenser end 40 is generally tapered with respect to the tubular body 20 and includes a pair of flexible tabs 46 that extend into the bore 44. The flexible tabs 46 are adapted to engage a portion of the screw-blade sets 16. The dispensing end 40 defines a hexagonal (keyed) opening 48 into the bore 44.

The cap end 42 is sized to be received within the opening 26 of the cap 18, and includes a reduced portion 50 having an outer diameter less than an inner diameter of the tubular body 20 whereby the reduced portion 50 fits within the opening 26. A circumferential groove 52 formed around the tubular body 20 at the insertion end 42 is sized to seat the ball detents 34.

With continued reference to FIGS. 1 and 2, the clip 14 includes tubular halves 60 and a push block 62. The tubular halves 60 are adapted to be assembled together to form a sheath and are received within the bore 44 of the body 12. Each tubular half 60 has a generally half-circle cross section, and when joined encapsulate the push block 62 and the plurality of screw-blade sets 16, as well as define a cavity 64. The cavity 64 may be generally hexagonal and extends along the axis A-A. A cavity slot 66 extends into the cavity 64 from the surface of the joined tubular halves 60 and parallel to the axis A-A. The cavity slot 66 is sized to receive a portion of the push block 62. As best seen in FIG. 4, the tubular halves 60 have a plurality of detents 68 formed in an inner surface defining the cavity 64. Each detent 68 has a sloped face 70 and a back wall 72. The detents 68 are sized to receive a portion of the push block 62.

The tube halves 60 may be made from a liquid crystal polymer, such as VECTRA®, available from Ticona, Inc., of Germany. It is to be appreciated, however, that various other materials may be used.

With reference again to FIGS. 1, 2, and 4 the push block 62 may include a hexagonally shaped block portion 74 sized to fit within the cavity 64. A pair of posts 76 extend out from the block portion 74 and end in a push pad 78. The posts 76 are sized to fit through the cavity slot 66 of the tubular halves 60 and the longitudinal slot 45 of the tubular body 20. The push pad 78 may include a rough grip surface designed to increase friction between the push pad 78 and the finger of a user of the dispensing apparatus 10. However, the push pad 78 may have various configurations and textures so long as it is operable by a user of the dispensing apparatus 10. As best seen in FIG. 4, the block portion 74 further includes a flexible tooth 80 extending therefrom. The flexible tooth 80 is sized to fit within the plurality of detents 68 of the clip 14 and provides a ratcheting feature.

Figure 3:
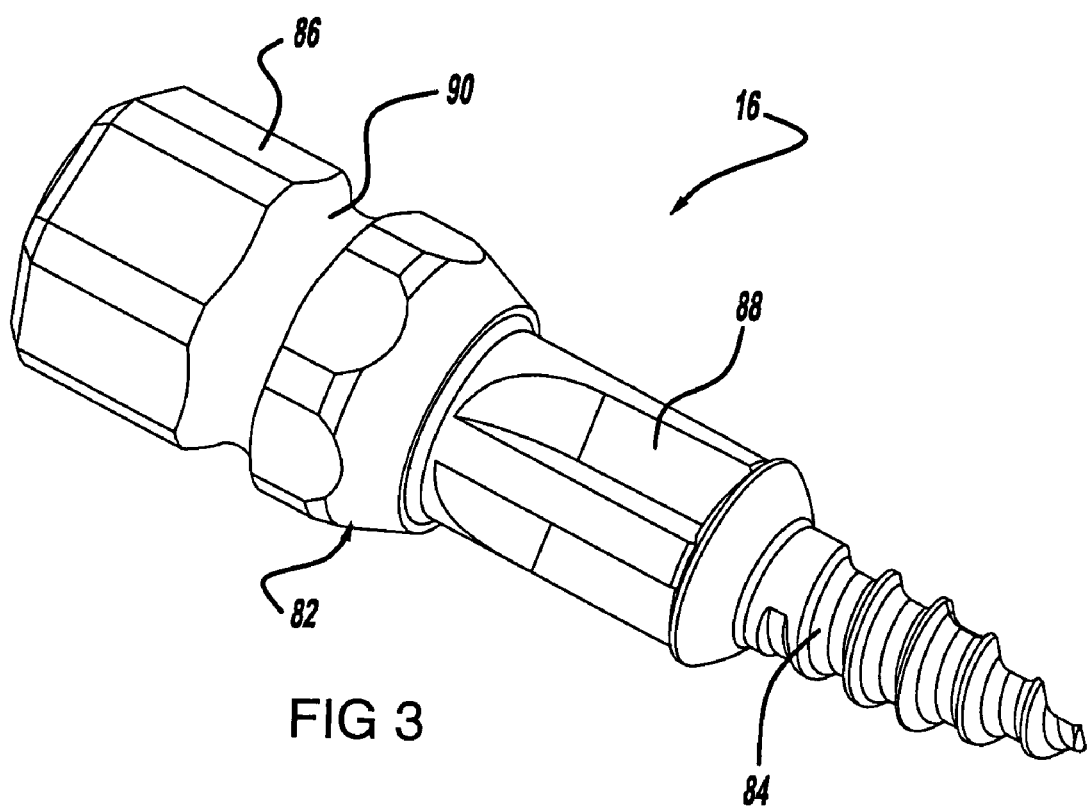
FIG. 3 is a perspective view of a screw-blade set shown in FIG. 2.

Referring to FIG. 3, each screw-blade set 16 includes a blade 82 and a screw 84. The blade 82 includes a head 86 and a neck portion 88 extending axially therefrom. As shown, the head 86 has a generally hexagonal shape matching the hexagonal shape of the cavity 64 of the clip 14. It is to be appreciated that the head 86 may have various other shapes, including for example, oval, triangular, star, square, pentagonal, or octagonal shapes. However, variations in the shape of the head 86 may require matching shapes in the cavity 64, the push block 62, and the opening 48 of the tubular body 20.

The head 86 includes a circumferential recess 90 formed in its outer surface sized to receive the tabs 46 of the tubular body 20. As best seen in FIG. 4, the head 86 further defines a screw receptacle 92 at one end thereof. The screw receptacle is sized to receive the screw 84 from an adjacent screw-blade set 16.

The neck 88 of the blade 82 is coupled to the screw 84. To assemble the screw-blade set 16, the screw 84 is press fitted to the neck 88. The screw-blade set 16 can be assembled in other ways, such as by welding, adhesive, or other bonding mechanism. The blade 82 may be made from stainless steel and the screw 84 may be made from any of a variety of bio-compatible materials, such as commercially pure titanium, grade 2 or 4. Other metals that may be implanted are, but not limited to, stainless steel or cobalt chrome molybdenum. Other examples of bio-compatible materials that may be used are the implantable plastics PEEK or PET.

In addition to being made from bio-compatible materials, the screw-blade sets 16 may also be made from a variety of bio-resorbable materials. The screw-blade sets 16 may be integrally formed with a joint between the screw 84 and blade 82 formed to shear at full insertion of the screw 84. One such resorbable material of particular interest is marketed by Biomet, Inc. (Warsaw, Ind.) under the tradename LACTOSORB®. LACTOSORB® is an absorbable co-polymer synthesized from all-natural ingredients: 82% L-lactic acid and 18% glycolic acid, and is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of its strength for six to eight weeks. Such a time period is appropriate for healing, but not so long as to raise concerns about long-term stress shielding of bone. In addition to LACTOSORB®, other resorbable materials may be used such as PLA, PGA, and others including various polymers, ceramics, etc.

With reference to FIGS. 1-4, the assembly of the dispensing apparatus 10 will now be described. The clip 14 is loaded by inserting a plurality of the screw-blade sets 16 into the cavity 64. The screws 84 point towards the dispensing end 40 of the tubular body 20. As noted above, the screws 84 fit within the screw receptacles 92 of adjacent screw-blade sets 16 to allow more screw-blade sets 16 to be loaded into the clip 14. When fully loaded, the push block 62 is disposed at one end of the clip 14 and abuts the blade 82 of the screw-blade set 16 positioned most distal the dispensing end 40 of the tubular body 20 while the tooth 80 of the push block 62 seats within a detent 68. For medical applications, the clip 14 and screw-blade sets 16 may be sterilized and packaged separately from the body 12.

The loaded clip 14 is inserted into the tubular body 20 such that the posts 76 of the push block 62 align with the longitudinal slot 45 formed in the tubular body 20. The push pad 78 is positioned adjacent the periphery of the body 12. The cap 18 is attached to the tubular body 20 by displacing the sleeve 24 so that the projections 38 no longer align with the ball detents 34, thus allowing the insertion end 42 to be inserted into the opening 26. The insertion end 42 may be keyed to the opening 26 such that the cap 18 and the tubular body 20 are rotationally locked together. By replacing the sleeve 24 to align the projection 38 with the ball detents 34, the ball detents 34 are urged into the opening 26 and engage the circumferential groove 52 of the tubular body 20, thereby securing the tubular body 20 to the cap 18.

Screws 84 are made ready for insertion into a material by moving the push block 62 in the direction of the dispensing end 40 of the tubular body 20. This forces the flexible tooth 80 to slide along ramped surface 70 of the detent 68. The push block 62 urges the plurality of screw-blade sets 16 along the axis A-A in the direction of the dispensing end 40 until the tooth 80 engages a succeeding detent 68 in the cavity 64. A back wall 72 prevents the push block 62 from moving toward the insertion end 42, thus providing a ratchet effect.

When the flexible tooth 80 of the push block 62 has engaged a detent 68, one of the screw-blade sets 16 is in a use position wherein the tabs 46 have engaged the circumferential recess 90 of the screw-blade set 16 positioned adjacent the proximate end and the screw 84 extends from the dispensing end 40. In this position the screw 84 is ready to be inserted into a material.

Rotation of the drive shaft 28 of the cap 18 rotates the tubular body 20. Because the blades 82 of the screw-blade sets 16 are keyed to fit within the hexagonal opening 48 of the tubular body 20, the screw-blade 82 (and thus the included screw 84) is likewise rotated. The drive shaft 28 may be rotated by a tool, which may be a hand-operated tool or powered driver having a connector adapted to receive the hexagonally shaped end 30. The powered driver may include multiple forward and reverse speeds to facilitate insertion and removal of screws 84. The tool may be fingertip actuated and held in a pencil-grip style, such as Power Driver, available from Walter Lorenz Surgical, Inc. of Jacksonville, Fla. The screwdriver is powered by a 6-volt lithium-ion battery pack, which is sold sterile. The drive shaft 28 may be rotated by various other means, for example by the hand of the user, or another tool such as a conventional screwdriver or pliers.

The screw 84 disengages from the blade 82 under sufficient rotational resistance, for example, at full insertion of the screw 84 in a material, at which time the coupling between the screw 84 and blade 82 is broken. A user may also rock the multiple screw delivery apparatus 10 after the screw 84 is seated within a material in order to decouple the screw 84 from the blade 82. The tabs 46 retain the blade 82 until such time as the push block 62 is again urged in the direction of the insertion end 42, wherein the next screw-blade set 16 ejects the blade 82 and is moved to the use position.

With reference to FIGS. 5-8, a multiple screw delivery apparatus is generally indicated by reference numeral 10'. The multiple screw delivery apparatus 10' is generally similar to the multiple screw apparatus shown in FIGS. 1-4, and includes a clip 14', 14", a screw set 16' (including screws 84' or screws 84"), and a dispenser end 40'. The screw 84' and the screw 84" differ in the configuration of the head portion, and similarly, the clip 14' and 14" differ in their internal geometry to accommodate respective screws 84', 84".

Figure 6:
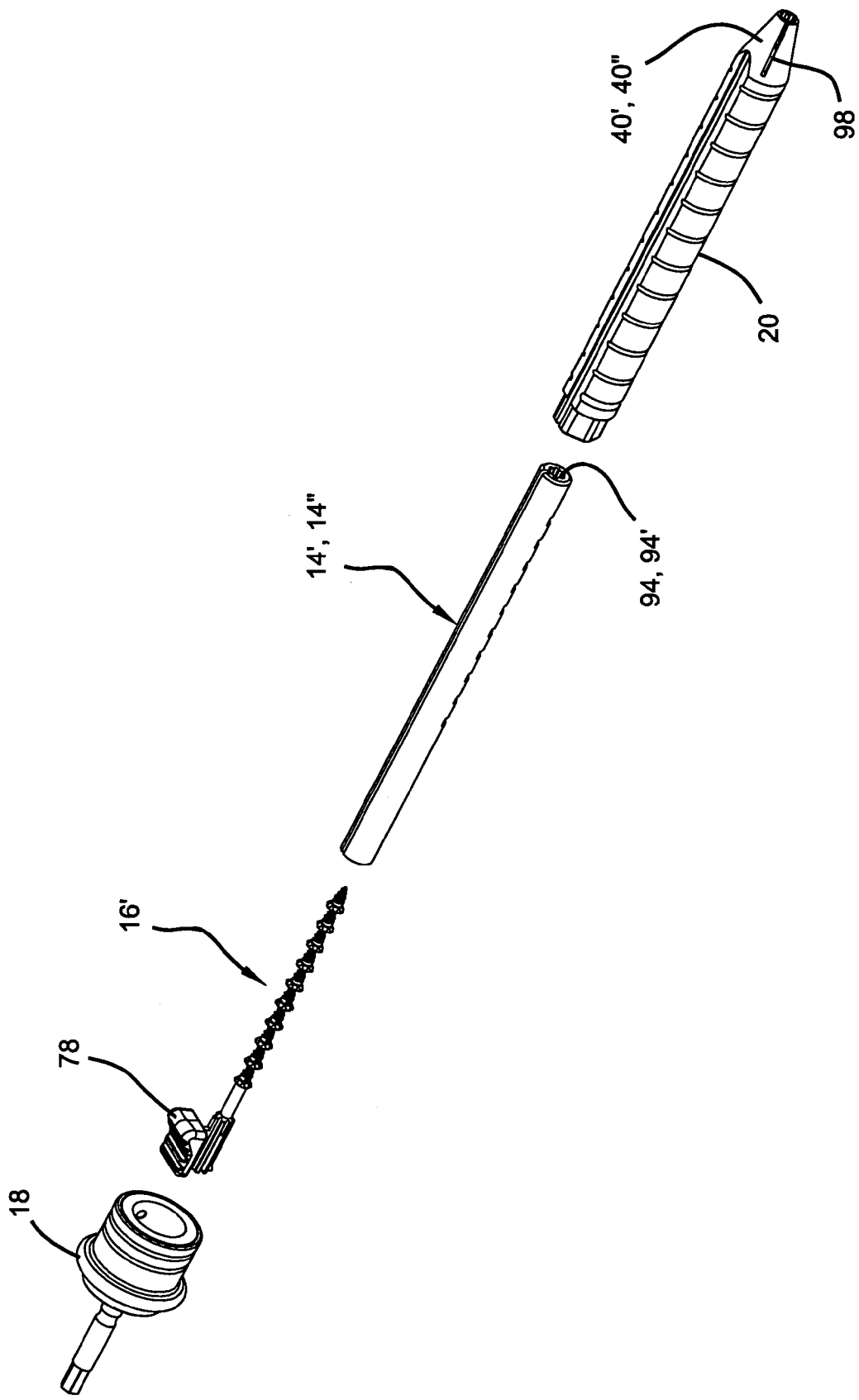
FIG. 6 is an exploded perspective view of the multiple screw delivery apparatus of FIG. 5.
Figure 7:
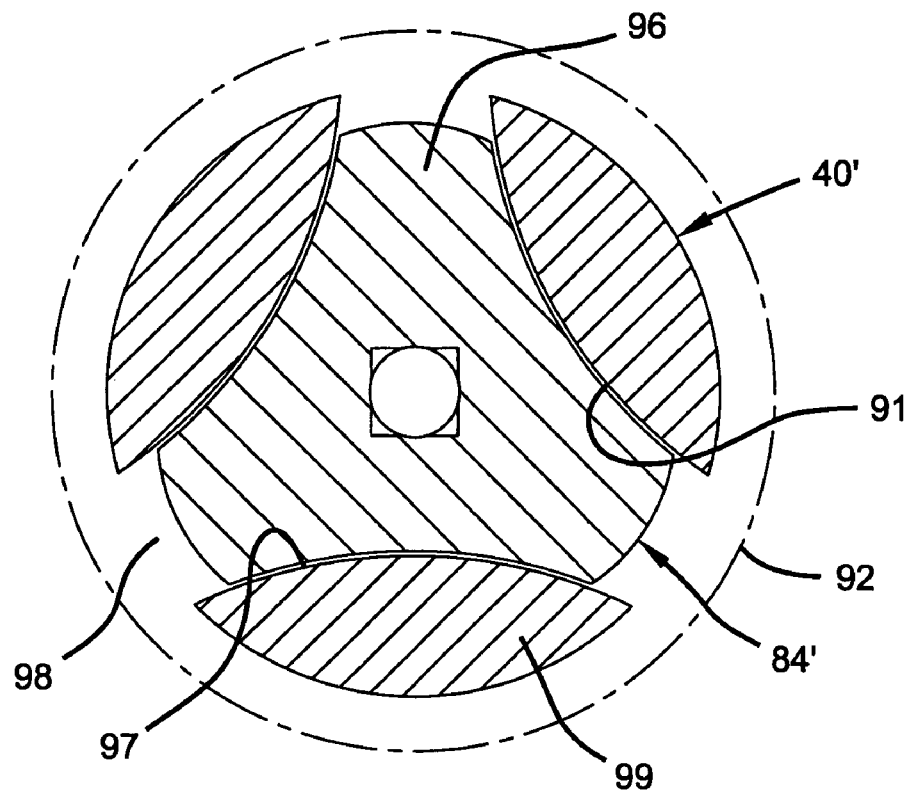
FIG. 7 is a cross-sectional schematic view of the multiple screw delivery apparatus of FIGS. 5 and 6.
Figure 8:
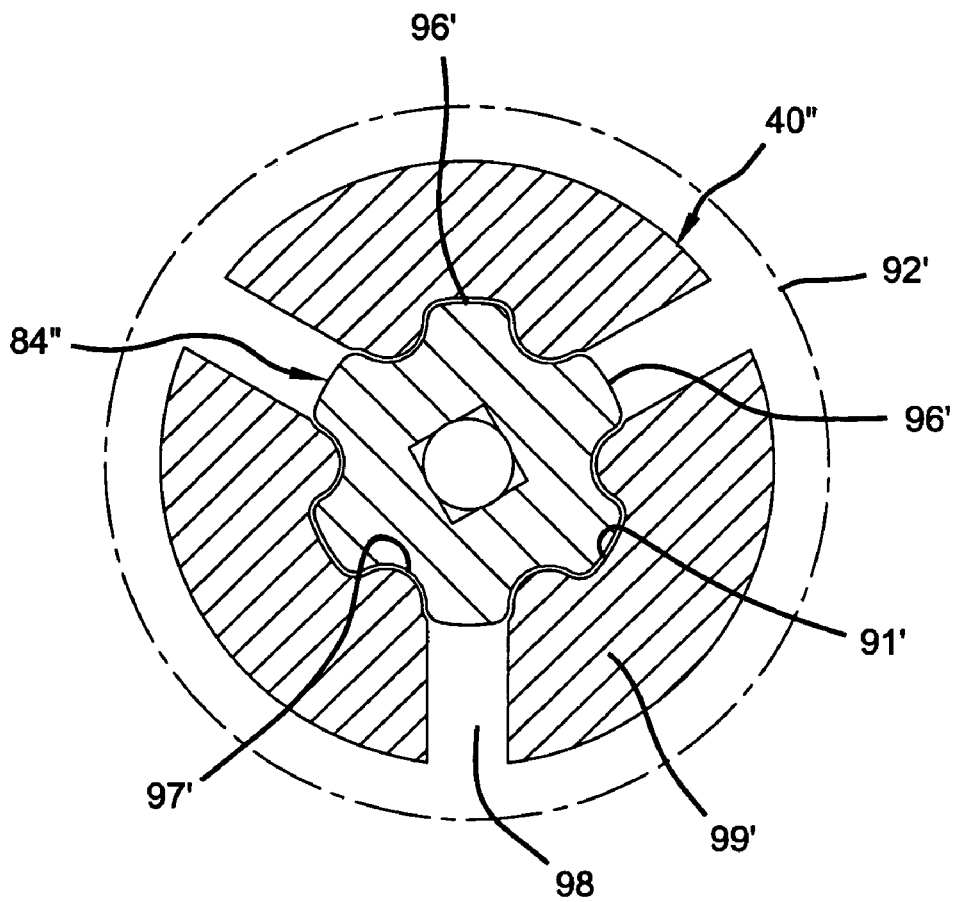
FIG. 8 is another cross-sectional schematic view of the multiple screw delivery apparatus of FIGS. 5 and 6.

As best shown in FIGS. 6-8, the screw set 16' includes screws 84', 84" nested within another screw 84', 84", respectively, in series. Accordingly, the screw set 16' may not require a blade 82 (as discussed previously and shown in FIG. 3) between succeeding screws 84', 84". Each screw 84', 84" may directly engage a succeeding screw 84', 84", respectively, as the push pad 78 is urged through the clip 14', 14", toward the dispenser end 40'.

Again referencing FIGS. 5-8, the clip 14', 14" and the dispensing end 40', 40" include an internal geometry suited to a particular screw 84', 84". The cavity 64 of clip 14', 14" is defined by rails 94, 94' spaced equidistantly and formed axially along an inner diameter surface of the clip 14', 14". The rails 94, 94' are received in grooves 97, 97' formed in a head portion of each of the screws 84', 84", respectively. The rails 94, 94' and grooves 97, 97' prevent the screws 84', 84" from rotating or misaligning while within the clip 14', 14".

With reference to FIG. 7, the screw 84' is a three-lobed screw, whereby the head portion 96 of the screw 84' includes three equidistantly-spaced lobes 96. In the clip 14', the grooves 97 between the lobes 96 align with the rails 94 of the clip 14'. As shown in FIG. 7, the lobes 96 are aligned with slits 98 in the dispensing end 40'.

With reference to FIG. 8, the screw 84" is a six-lobed screw, wherein the head portion includes six lobes 96'. The clip 14" includes rails 94' and slots 95' accommodating the grooves 97' and lobes 96' of the screw 84", respectively. As shown in FIG. 8, the lobes 96' are alternately aligned with channels 91' and slits 98. It should also be recognized that various other screw designs may be employed with the present invention by varying the arrangement of rails 94, 94', slots 95, 95', grooves 97, 97' and slits 98.

With reference to FIGS. 7 and 8, the dispensing end 40', 40" is generally tapered with respect to the tubular body 20, includes a geometrical tip (or keyed) opening 92, 92', and three slits 98. The opening 92, 92' allows the passage of screws 84', 84" as they are passed from the clip 14', 14" and generally includes lobes 99, 99' operable to position the screws 84', 84" for use. As shown in FIG. 7, the lobes 99 of the opening 92 have a generally convex surface 91 for alignment with the grooves 97 of the screw 84'. As shown in FIG. 8, the lobes 99' of the opening 92' include a channel 91' for alignment with the lobes 96'.

The apparatus 10', through the cooperating geometries of the screws 84', 84", dispensing end 40', 40" and clip 14', 14", maintain alignment of the screws 84', 84" within the body 20 and fix the screws 84', 84" for rotation with the apparatus 10'. The slits 98 extend axially from the tip opening 92 along the tubular body 20 and allow the dispensing end 40', 40" to deflect away from the screws 84', 84" as the screws are dispensed from the multiple screw delivery apparatus 10', whereby the screws 84', 84" are quickly released from the dispensing end 40', 40" when enough force is applied thereto.

Figure 9:
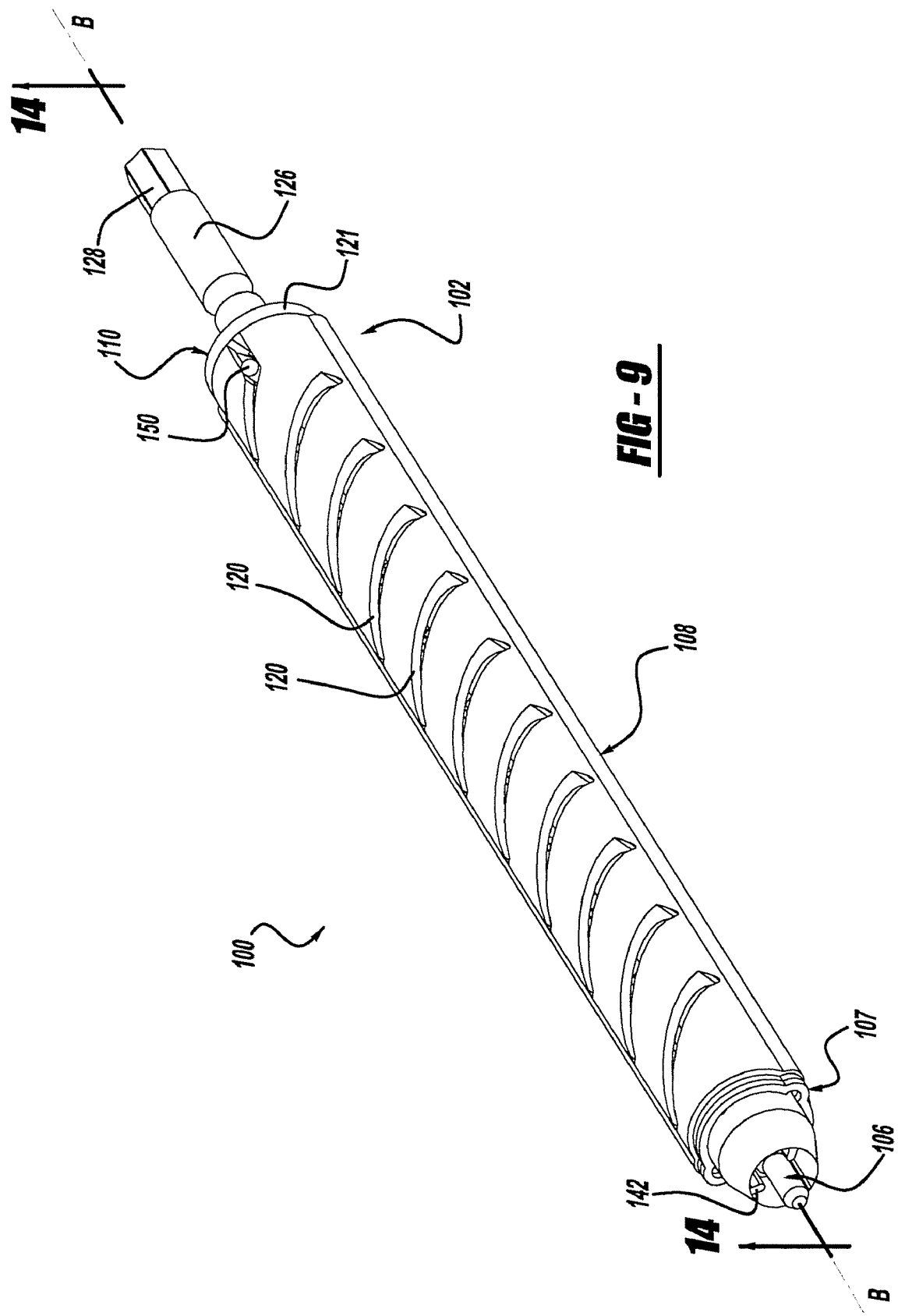
FIG. 9 is a perspective view of a multiple screw delivery apparatus according to the present teachings.

Turning now to FIGS. 9 and 10, a multiple screw delivery apparatus is indicated generally by reference numeral 100. The delivery apparatus 100 includes a body 102 with a longitudinal axis indicated by line B-B. The body 102 is sized to receive a clip 104. A plurality of screw-blade sets 106 are sized to fit within the clip 104. A stopper ring 107 is mounted to the clip 104. Rotation of the clip 104 relative to the body 102 urges the screw-blade sets 106 to be positioned for use and subsequently ejected from the clip 104.

Figure 14:
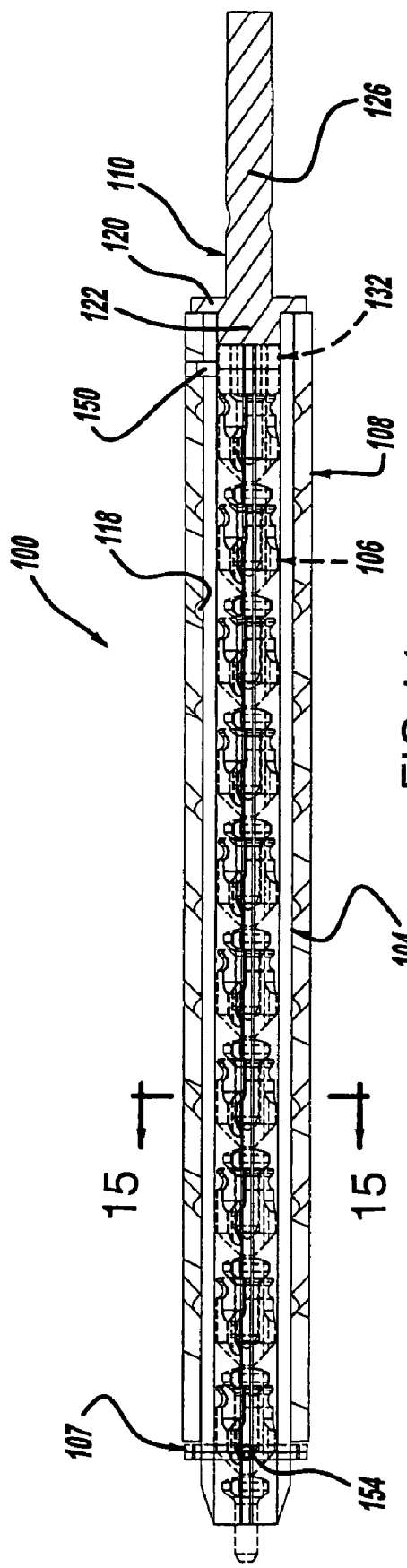
FIG. 14 is a cross-sectional view of the screw delivery apparatus taken in the direction of arrow 14-14 in FIG. 9.

The body 102 includes a tubular portion 108 with a cap 110 attached thereto. The tubular portion 108 includes a dispensing end 112 and a cap end 114. The tubular portion 108 further defines a bore 116 that extends from the dispensing end 112 to the cap end 114 along an axis B-B. The bore 116 is sized to receive the clip 104. As best seen in FIG. 14, a spiral groove 118 formed in the bore 116 runs from the cap end 114 to adjacent the dispensing end 112 along the axis B-B. The cutouts 120 extend from the outside of the tubular portion 108 into the bore 114 and form the groove 118. The spiral groove 118 receives a portion of the clip 104, as will be described below.

The cap 110 includes circular base 121 with a lug 122 extending from an end thereof. The lug 122 includes notches 124 that engage the clip 104 and rotationally fix it relative to the cap 110. A drive shaft 126 extends out from an opposite side of the cap 110 along the axis B-B. The drive shaft 126 may include a hexagonally shaped end 128 adapted to be received within a tool such as those described above.

With continued reference to FIG. 10, the clip 104 includes a sheath 130 and a slide block 132. The sheath 130 has a cap end 134 and a dispensing end 136 and is sized to fit within the bore 116 of the tubular portion 108. The sheath 130 defines a cavity 138 that extends along axis B-B from the cap end 134 to the dispensing end 136. A longitudinal slot 140 extends from the surface of the sheath 130 into the cavity 138 and from the cap end 134 parallel to the axis B-B and adjacent the dispensing end 136. The cavity 138 includes rails 142 that extend along the length of the cavity 138. The rails 142 are sized to engage the screw-blade sets 106 and ride within the notches 124 of the cap 110. The longitudinal slot 140 is sized to receive a portion of the stopper ring 107.

The clip 104 may be formed from a liquid crystal polymer, for example VECTRA® as described above. Another material may be stainless steel. However, various other materials may be employed.

Figure 11:
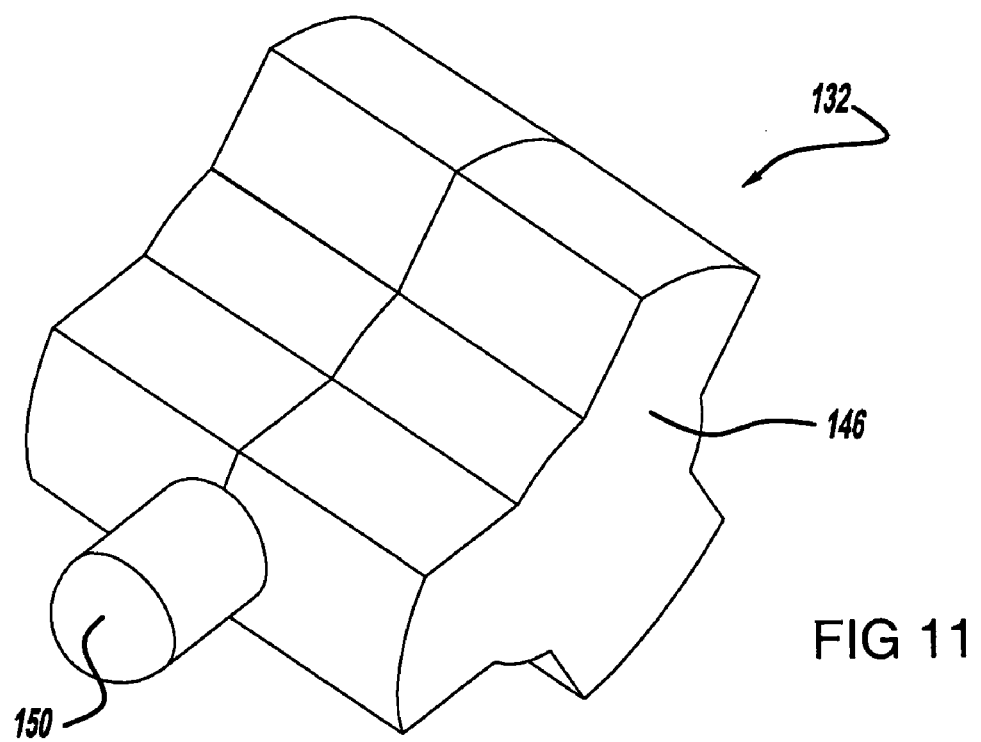
FIG. 11 is a perspective view of a slide block shown in FIG. 10.

With reference now to FIG. 11, the slide block 132 includes a block body 146 having cutouts 148 sized to receive the rails 142 of the sheath 130. A post 150 extends out from the block body 146 and is received within the longitudinal slot 140 (FIG. 10) and the spiral groove 118 (FIG. 9). The slide block 132 engages the screw-blade sets 106 and urges them to a use position and subsequently ejects them from the dispensing apparatus 100.

With reference to FIG. 12, the stopper ring 107 includes a ring portion 152 received on the dispensing end 136 of the sheath 130. A stopper 154 extends radially inward from the inner diameter surface of the ring portion 152 and is received within the longitudinal slot 140 in the clip 104. The stopper 154 engages the screw-blade set 106 positioned most proximate to the dispensing end 136.

Figure 13:
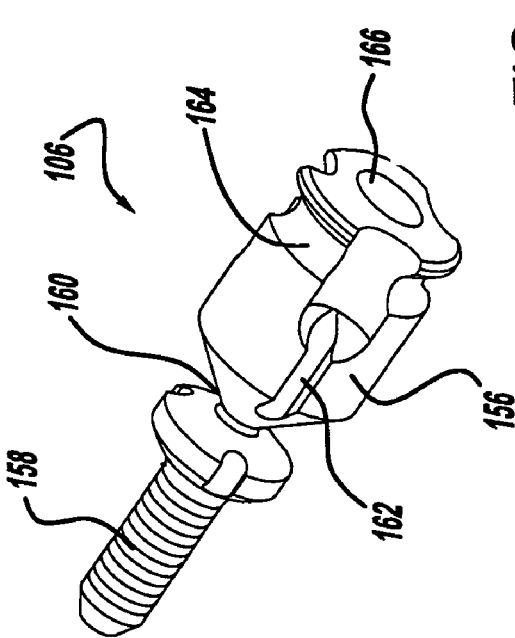
FIG. 13 is an enlarged perspective view of a screw-blade set shown in FIG. 10.

Referring now to FIG. 13, the screw-blade set 106 includes a blade 156 and a screw 158 coupled by a neck portion 160, which may include a reduced cross-sectional area. The blade 156 has grooves 162 formed therein and adapted to receive the rails 142. A circumferential recess 164 formed in the outer surface of the blade 156 receives the stopper 154 (FIG. 12). At one end thereof, the blade 156 includes a screw receptacle 166 for receiving the screw 158 from a separate, adjacent screw-blade set 106.

The blade 156, the screw 158, and the neck portion 260 may be formed unitarily from a bio-resorbable material, for example LACTOSORB® as described above. The blade 156 and the screw 158, however, may be formed from a variety of bio-compatible materials. Further, the blade 156 and screw 158 may be joined in any other manner, such as those discussed above.

Figure 15:
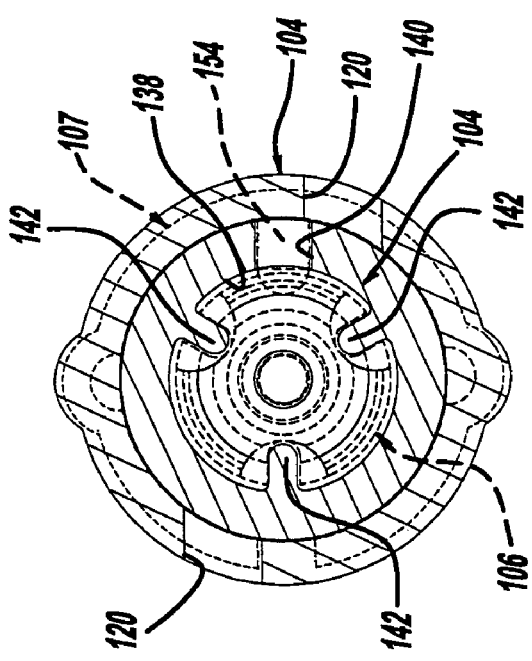
FIG. 15 is a cross-sectional view of the multiple screw delivery apparatus taken along line 15-15 in FIG. 14.
Figure 16:
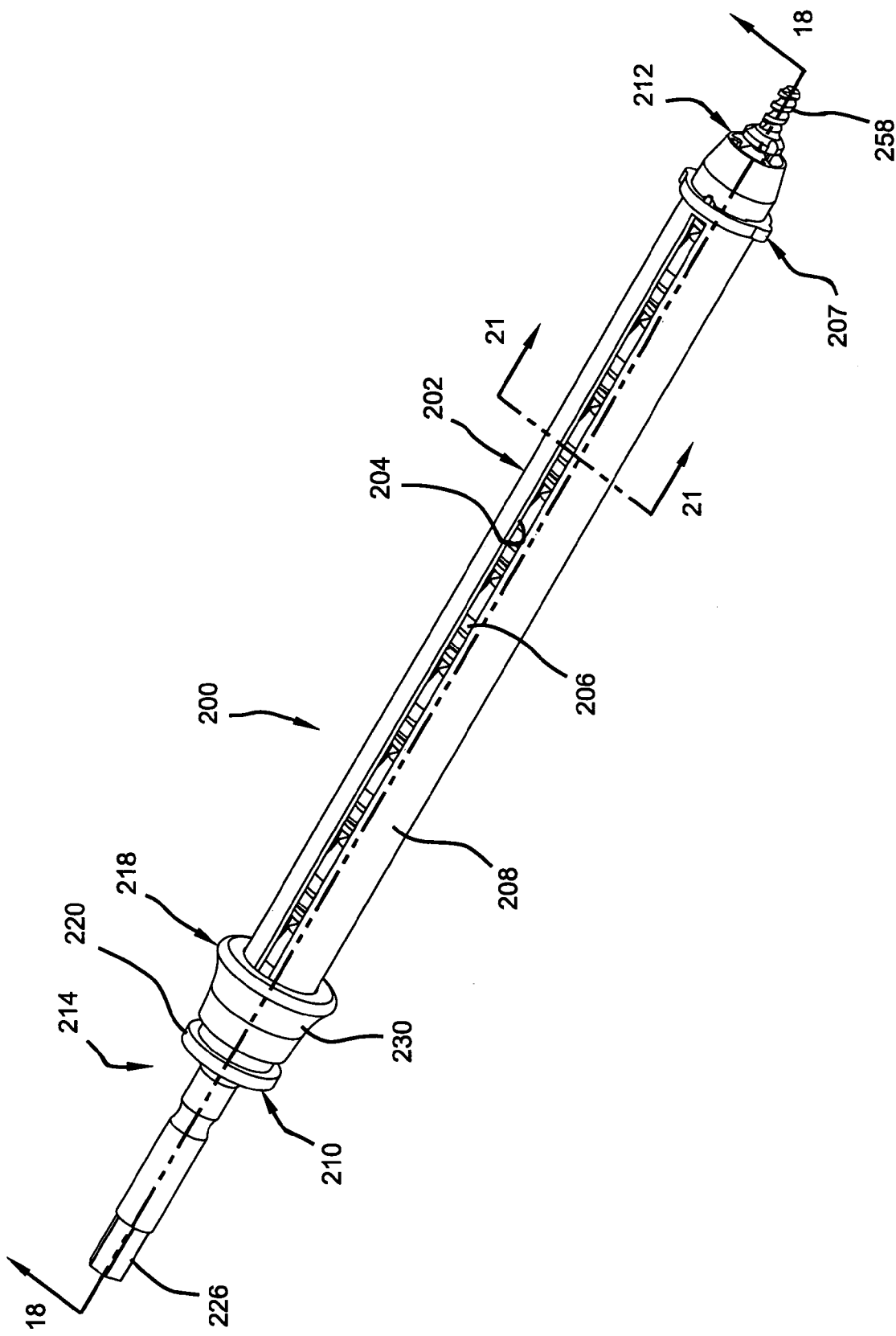
FIG. 16 is a perspective view of a multiple screw delivery apparatus according to the present teachings.

With continued reference to FIGS. 9-13, and more particularly to FIGS. 14 and 15, the assembly of the dispensing apparatus 100 will now be described. The clip 104 is loaded by inserting a plurality of the screw-blade sets 106 into the cavity 138. The rails 142 slide within the grooves 162 of the blade 156 (FIG. 15). The screws 158 are received within the screw receptacles 166 of adjacent screw-blade sets 106 to allow more screw-blade sets 106 to be loaded into the clip 104. When fully loaded, the push block 132 is disposed at the cap end 114 of the sheath 130, post 150 extends through the longitudinal slot 140 of the sheath 130, and the block body 146 abuts the blade 156 of the screw-blade set 106 most proximate to the dispensing end 136.

The loaded clip 104 is inserted into the tubular portion 108 such that the post 150 of the push block 132 extends into the spiral groove 118 and the loaded screws 158 point towards the dispensing end 112 of the tubular portion 108. The cap 110 is then attached to the loaded clip 104 such that the notches 124 receive the rails 142 to rotationally lock the clip 104 to the cap 110. The stopper ring 107 is fitted around the sheath 130 such that the stopper 154 extends through the longitudinal slot 140 into the cavity 138.

The screws 158 are made ready for insertion into a material by rotating the tubular portion 108 relative to the cap 110 and the clip 104, which, in turn, causes the post 150 and the slide block 132 to move along the axis B-B because the post 150 is constrained by the spiral groove 118 and the longitudinal slot 140. The slide block 132 urges the loaded screw-blade sets 106 along the axis B-B in the direction of the dispensing end 136 of the sheath 130 until the stopper 154 engages the circumferential recess 164 formed in the blade 156 of the screw-blade set 106 positioned proximate the dispensing end 136. In this position, the screw 158 extends from the dispensing end 136 and is ready to be inserted into a material.

Rotation of the drive shaft 126 rotates the sheath 130, which through rails 142 rotates the screw-blade sets 106. The screw 158 disengages from the blade 156 under sufficient rotational resistance at which time the neck portion 160 may be sheared from an increased shear stress due to its reduced cross sectional area. The stopper 154 retains the remaining blade 156 until such time as the tubular portion 108 is again rotated relative to the cap 110 and the slide block 132 urges a new screw-blade set 106 into an extended or use position and ejects the spent blade 156.

Turning now to FIGS. 16-21, a multiple screw delivery apparatus is indicated generally by reference numeral 200 and includes a body 202 adapted to receive a plurality of screw-blade sets 206, each including a blade 256 and a screw 258 connected by a neck portion 260. A stopper ring 207 is mounted to the body 202 and is positioned to releasably retain the screw-blade set 206 in position for use. A pusher 218 is mounted to the clip 204 at an end opposite the stopper ring 207 and is slidably moveable along the body 202 toward the stopper ring 207 to urge one of the screw-blade sets 206 into position for use and to subsequently eject used blades 256 from the body 202.

The body 202 includes a tubular portion 208, which includes a dispensing end 212 and a cap end 214. A cap 210 covers the cap end 214 of the tubular portion 208, and may be integrally formed with the body 202 or fixedly attached. The tubular portion 208 defines a cavity 216 that may extend from the dispensing end 212 to the cap end 214, and which is sized to receive one or more screw-blade sets 206. A groove 204 formed in the tubular portion 208 extends axially from the cap end 214 to adjacent the dispensing end 212, into the cavity 216, and slidably receives a portion of the pusher 218.

The cap 210 includes a circular base 220 rotationally fixed to the body 202. A drive shaft 226 extends from the cap 210 in a direction opposite from the dispensing end 212. The drive shaft 226 may include a hexagonally-shaped end 228 adapted to be received within a tool such as those described above.

Figure 17:
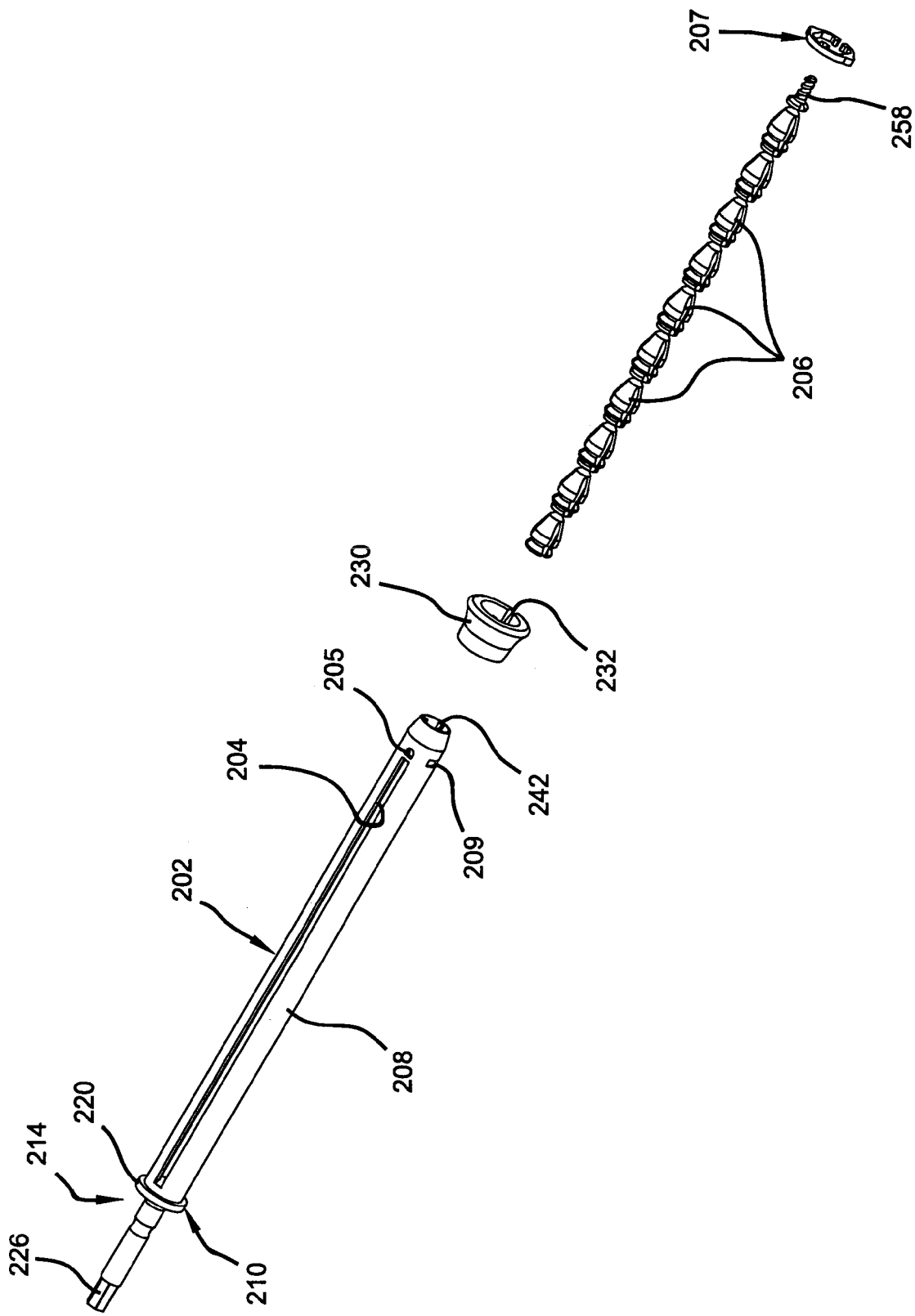
FIG. 17 is an exploded perspective view of the multiple screw delivery apparatus of FIG. 16.
Figure 18:
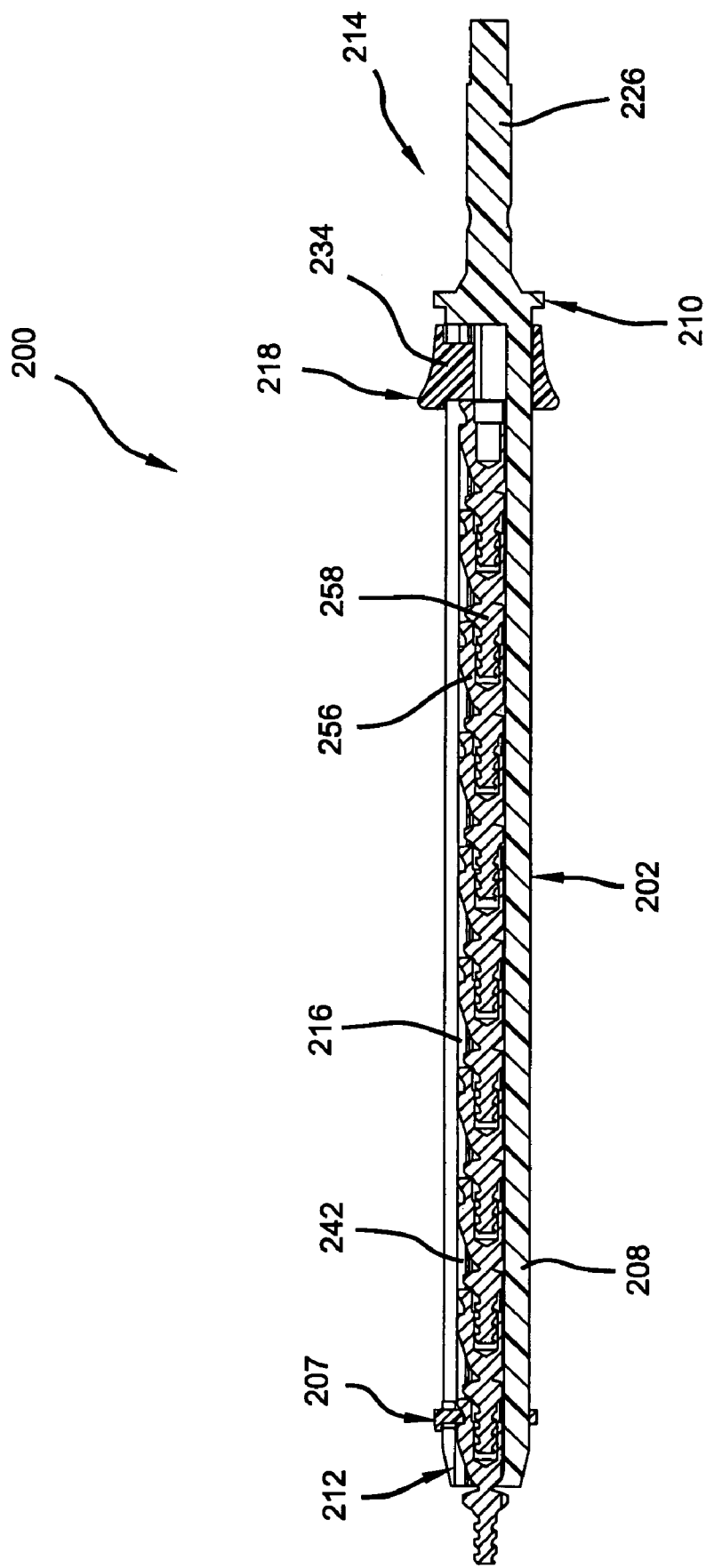
FIG. 18 is a cross-sectional view of the multiple screw delivery apparatus taken along line 18-18 in FIG. 16.
Figure 20:
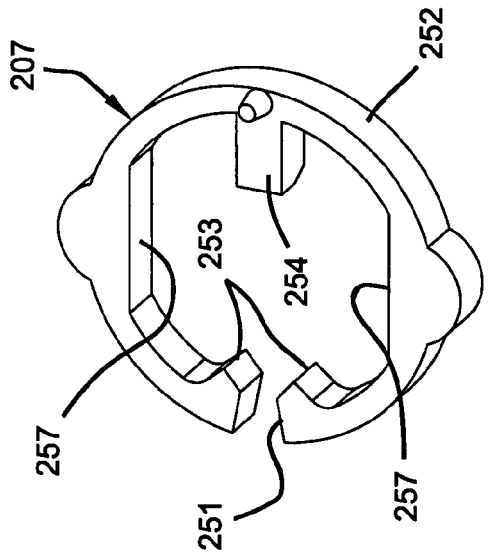
FIG. 20 is a perspective view of a stop ring shown in FIGS. 16-18.
Figure 21:
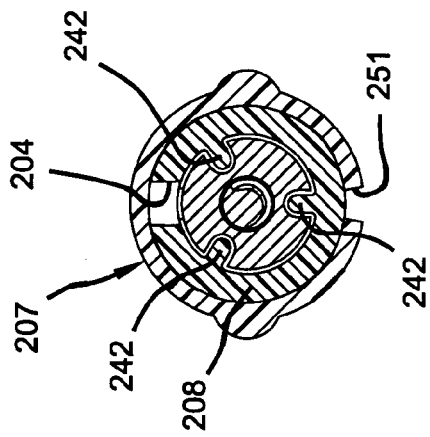
FIG. 21 is a cross-sectional view of the multiple screw delivery apparatus taken along line 21-21 in FIG. 16.
Figure 19:
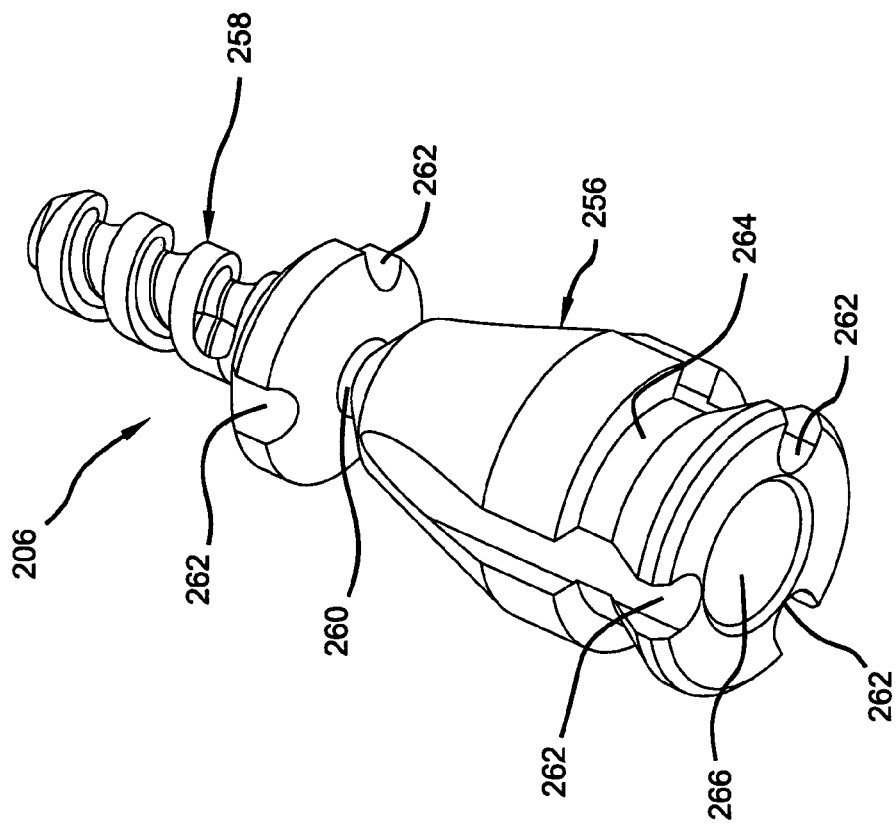
FIG. 19 is a perspective view of a screw-blade set shown in FIGS. 16-18.

With reference to FIGS. 17 and 18, the pusher 218 includes a cylindrical body 230 having a slot 232 axially formed through the body and a block 234 extending radially inward along an inner diameter surface of the body 230 diametrically opposite the slot 232. The push block 234 is shaped to abut and slide the screw-blade sets 206 within the body 202, sequentially advancing one of the screw-blade sets 206 to the use position. As shown, the push block 234 extends through the slot 204 to engage an end portion of a blade 256 of the screw-blade set 206 most distant to the dispensing end 212.

The tubular portion 208 of the body 202 includes rails 242 that extending along the length of the inner diameter of the tubular portion 208 and adapted to engage the screw-blade sets 206. The blade 256 and the screw 258 include grooves 262 formed therein to receive the rails 242. A circumferential recess 264 is formed in the outer surface of the blade 256 and receives the stopper ring 207, depending on the position of the blade 256 in the series of screw-blade sets 206. The push block 234 abuts the blade 256 most distant from the dispensing end 212 and sequentially urges the series of screw-blade sets 206 to a use position, and subsequently ejects used blades 256 from the apparatus 200.

The blade 256, the screw 258 and the neck portion 260 may be formed unitarily from a bio-resorbable material, for example, LACTOSORB®, as described above. The blade 256 and the screw 258, however, may be formed from a variety of bio-compatible materials. Further, the blade 256 and the screw 258 may be joined in any other manner, such as those discussed above.

The stopper ring 207 includes a ring portion 252 having a slot 251 formed through the body and a stopper 254 disposed radially inward from an inner diameter surface of the body 252 approximately diametrically opposed to the slot 251. Flats 257 are formed along an inner diameter surface of the ring portion 252 between the slot 251 and stopper 254. The slot 251 is flanked by hooks 253, which secure the stopper ring 207 to the body 202 through engagement with hook openings (not shown) through a surface of the body 202 generally opposite an aperture 205 adapted to receive the stopper 254. The stopper ring 207 is fitted around the tubular portion 208 of the body 202, the stopper 254 extends through the aperture 205 to selectively engage a screw-blade set 206, and the flats 257 seat in slots 209 formed on the body 202 between the aperture 205 and hook openings (not shown).

With continued reference to FIGS. 16-21, the assembly of the dispensing apparatus 200 will now be described. The pusher 218 is placed on the body 202 with the push block 234 extending into the cavity 216 through the slot 204. The body 202 is loaded by inserting a plurality of the screw-blade sets 206 into the cavity 216 of the tubular portion 208 through the dispensing end 212. The rails 242 slide within the grooves 262 of the screw-blade sets 206. The screws 258 are received in the screw receptacles 266 of adjacent screw-blade sets 206 to allow a greater number of screw-blade sets 206 to be loaded into the body 202. Once fully loaded, the push block 234 of the pusher 218 abuts the blade 256 of the screw-blade set 206 most distant from the dispensing end 212.

The stopper ring 207 is fitted around the body 202 with the stopper 254 extending through aperture 205 and hooks 253 received by openings 209 to retain the series of screw-blade sets 206 within the tubular portion 208. The screws 258 are ready for insertion into a material by rotating the tubular portion 208 through rotation of the drive shaft 226 rotationally fixed thereto via the cap 210. The pusher 218 urges the loaded screw-blade sets 206 toward a dispensing end 212 until the stopper 254 of the stop ring 207 engages the circumferential recess 264 formed in the blade 256 of the screw-blade set 206 positioned proximate the dispensing end 212. The screw 258 extending from the dispensing end 212 is ready to be inserted into a material by rotation of the body 202, such as by rotation of the drive shaft 226. The screw 258 may disengage from the blade 256 under sufficient rotational resistance, at which time the neck portion 260 may be sheared from an increased shear stress due to its reduced cross-sectional area. The stopper 254 retains the remaining blade 256 until such time as the pusher 218 is again urged toward the dispensing end 212 to locate a new screw-blade set 206 in the use position and eject the spent blade 256.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A multiple screw dispensing apparatus comprising:
   a tubular body having a first slot;
   a clip having a second slot and received in the tubular body wherein the first and second slots are substantially aligned and the clip has a plurality of detents formed therein;
   a screw set disposed within the clip, and including at least one screw releasably coupled to another screw;
   a block slidably mounted with respect to the body, and abutting the screw set, the block having a tooth sized to engage the detents as the block moves relative to the clip; and
   a push pad connected to the block through the first and second slots.

2. The multiple screw dispensing apparatus of claim 1, wherein the screw set includes a screw and a blade, wherein each pair of screw and blade is releasably coupled to another pair of screw and blade.

3. The multiple screw dispensing apparatus of claim 1, wherein the push pad extends laterally from the body.

4. The multiple screw dispensing apparatus of claim 1, wherein the body includes a keyed opening and the screws of the screw set have a cross section keyed to the keyed opening.

5. A multiple screw dispensing apparatus of claim 4, wherein the keyed opening has a plurality of lobes sized to engage a head portion of a respective screw of the screw set.

6. The multiple screw dispensing apparatus of claim 1 wherein the block directly engages the screw set and concurrently advances an equivalent distance axially with the screw set during advancement of the block.

7. The multiple screw dispensing apparatus of claim 1, further comprising a cap disposed on the tubular body and including a rotatable drive shaft.

8. A multiple screw dispensing apparatus comprising:
   a body having a tube portion and defining a keyed opening;
   a plurality of screw blade sets loaded within the body and fixed within the opening for concurrent rotation with the body, the plurality of screw blade sets including at least a first screw set releasably coupled to a second screw set, wherein each of the first and second screw set is composed of a screw releasably coupled to a blade and wherein the screw defines a low-profile head having a first outer diameter and the blade defines a second outer diameter greater than the first outer diameter, and wherein a respective blade of a screw set in a use position has a cross-section that is keyed with the opening for concurrent rotation therewith;
   a clip received in the tube portion of the body and retaining the plurality of screw blade sets and having a plurality of detents formed therein;
   a block slidably mounted to the body and having a tooth sized to engage the detents as the block moves relative to the clip; and
   a push pad connected to the block and extending laterally from the body.

9. The multiple screw dispensing apparatus of claim 8, wherein the body includes a cap disposed thereon, the tube portion sized to receive the plurality of screw blade sets and secured by the cap.

10. The multiple screw dispensing apparatus of claim 8, further comprising a first slot formed in the body and a second slot formed in the clip, the push pad connected to the block through the first and second slots.

11. The multiple screw dispensing apparatus of claim 8, wherein the keyed opening has a plurality of lobes sized to engage a head portion of the respective blades.

12. The multiple screw dispensing apparatus of claim 8 wherein the cross-section is defined at a respective head of the blades and is non-circular.

13. The multiple screw dispensing apparatus of claim 12 wherein the cross-section defines one of hexagonal, oval, triangular, star, square, pentagonal and octagonal.

14. The multiple screw dispensing apparatus of claim 8 wherein the keyed opening imparts torque onto the respective blade.

15. The multiple screw dispensing apparatus of claim 8, further comprising a block slidably mounted with respect to the body, the block abutting the plurality of screw blade sets.

16. A multiple screw dispensing apparatus comprising:
a body defining an opening and a first slot;
a clip received in the body and defining a second slot and having a plurality of detents formed therein;
a plurality of screw blade sets loaded within the clip and fixed within the opening for concurrent rotation with the body, the plurality of screw blade sets including at least a first screw set releasably coupled to a second screw set, wherein each of the first and second screw set comprises a screw releasably coupled to a blade and wherein the screw defines a low-profile head having a first outer diameter and the blade defines a second outer diameter that is greater than the first outer diameter, and wherein a respective blade of a screw set in a use position is fixed for concurrent rotation with the opening;
a block slidably mounted with respect to the body, the block abutting the plurality of screw blade sets and having a tooth sized to engage the detents as the block moves relative to the clip; and
a push pad connected to the block through the first and second slots and extending laterally from the body.

17. The multiple screw dispensing apparatus of claim 16, wherein the opening is keyed and the respective blades each have a cross-section keyed to the keyed opening.

18. The multiple screw dispensing apparatus of claim 17, wherein the keyed opening has a plurality of lobes sized to engage a head portion of the respective blades.

19. The multiple screw dispensing apparatus of claim 17 wherein the respective blades are keyed to the opening at a non-circular cross-section thereof.

20. The multiple screw dispensing apparatus of claim 16 wherein the opening imparts torque onto the respective blade.

* * * * *